United States Patent [19]

LeVahn

[11] Patent Number: 5,080,088
[45] Date of Patent: Jan. 14, 1992

[54] FLEXIBLE RETRACTOR

[75] Inventor: Bruce A. LeVahn, New Brighton, Minn.

[73] Assignee: Minnesota Scientific, Inc., Minneapolis, Minn.

[21] Appl. No.: 118,477

[22] Filed: Nov. 9, 1987

[51] Int. Cl.[5] ............................................. A61B 17/02
[52] U.S. Cl. ...................................................... 128/20
[58] Field of Search ................. 128/3, 15, 17, 20, 321, 128/132 R, 17, 18

[56] References Cited

U.S. PATENT DOCUMENTS

| 1,947,649 | 2/1934 | Kadavy ................................. 128/20 |
| 3,372,696 | 3/1968 | Rudie ................................... 128/132 |
| 3,467,079 | 9/1969 | James .................................... 128/20 |
| 3,522,800 | 8/1970 | Lesser .................................... 128/20 |
| 3,749,088 | 7/1973 | Kohlmann .............................. 128/20 |
| 4,048,987 | 9/1977 | Hurson ................................... 128/20 |
| 4,155,355 | 5/1979 | Yamamoto ............................. 128/20 |
| 4,190,042 | 2/1980 | Sinnreich .............................. 128/20 |

FOREIGN PATENT DOCUMENTS 2730164 8/1978 Fed. Rep. of Germany ........ 128/20

Primary Examiner—Edward M. Coven
Attorney, Agent, or Firm—Kinney & Lange

[57] ABSTRACT

A retractor apparatus includes a retractor blade having a malleable element that defines a blade perimeter and a retractor area. A flexible member is supported by the malleable element and extends over the retractor area.

21 Claims, 1 Drawing Sheet

FLEXIBLE RETRACTOR

BACKGROUND OF THE INVENTION

1. Field of the Invention.

The present invention relates to surgical retractor apparatus, and in particular, it relates to a retractor used to retract organs.

2. Description of the Prior Art.

Surgical retractors are customarily used during major surgery to hold back the incision area to expose the area in which the surgeon operates. Abdominal surgery presents particular problems because of the presence of large soft organs, especially long lengths of intestines. The positioning during surgery of these lengths of intestines is vitally important to the success of the surgery. The intestines can obscure the surgeon's vision if the intestines are not held back by retractors. On the other hand, the intestines themselves are fragile and puncture results in contamination of the field of surgery greatly increasing the risk of post-operative infection.

In the prior art, surgical absorbent clothes or sponges, sometimes with the addition of hard metal retractors, have been used to hold and separate the intestines from the point of surgery.

The Rudie U.S. Pat. No. 3,372,696 describes the use of an abdominal pad having a flexible body member having a slight degree of rigidity with a weighted pocket formed at one end for holding back the intestines.

The Kohlmann U.S. Pat. No. 3,749,088 describes a retractor having a blade with a lower flexible end portion.

The Hurson U.S. Pat. No. 4,048,987 describes a hand-shaped retractor with a wire core having a multi-member body portion and a handle portion. The members of the body portion are individually adjustable.

The James U.S. Pat. No. 3,467,079 describes a retractor having a shaft that ends in a hook and a winged blade.

The Kadavy U.S. Pat. No. 1,947,649 describes a surgical instrument having a pair of pivotally connected members having a pair of outwardly extending arms that are inserted into a rubber covering. The arms are extended outwardly so that the covering is held taut between the two arms.

The Sinnreich U.S. Pat. No. 4,190,042 describes a flexible retractor having a bifurcated member with a flexible membrane tensed between segments of the bifurcated member.

The LeVahn U.S. Pat. No. 4,355,631 illustrates conventional retractors.

SUMMARY OF THE INVENTION

A retractor apparatus includes a retractor blade having a malleable element that defines a blade perimeter and a retractor area. A flexible member is supported by the malleable element and extends over the retractor area.

DETAILED DESCRIPTION OF THE PREFERRED EMBODIMENTS

Figure 1:
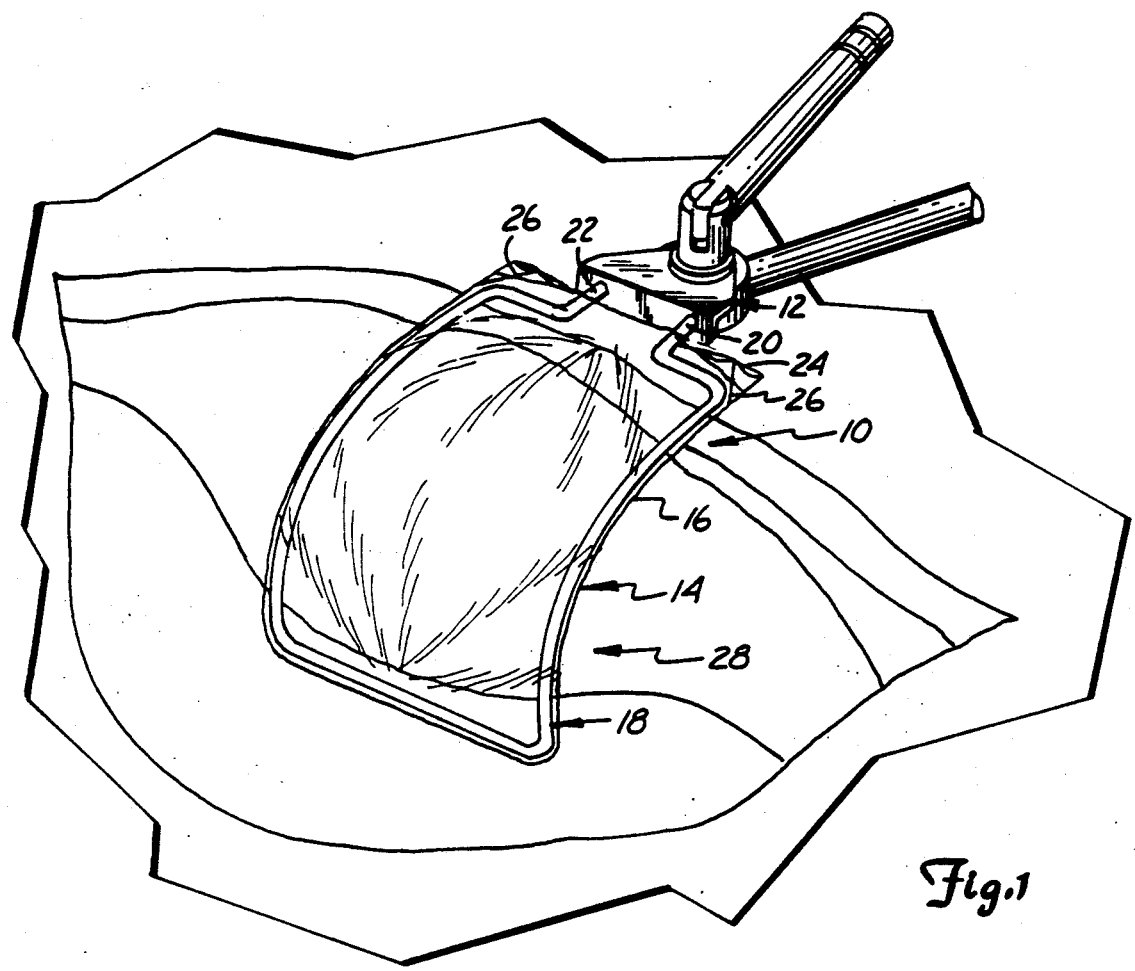
FIG. 1 is a perspective view of the retractor apparatus of the present invention, in its position of use, the retractor apparatus being supported by a retractor support.

In the drawings, like reference characters will be used to indicate like elements throughout the several views. A retractor device of the present invention is generally indicated at 10 in FIG. 1. The retractor 10 includes a blade 14 attached to a support member 12. The blade 14 includes a transparent membrane 16 supported by a wire element 18 in the form of a continuous loop. The wire element 18 has first and second ends 20 and 22 that are attached to the support member 12. Although the wire element 18 is shown in substantially rectangular form, the wire element may take various other shapes and be within the scope of the invention.

In the embodiment illustrated, the transparent membrane 16 is in the form of a bag having an open end 24. The wire element 18 is disposed within the bag forming the blade 14. The wire element 18 is inserted into the open end 24 and the open end 24 is heat sealed along the lines indicated by reference character 26. Alternatively, the membrane 16 need not be in the form of a bag. The membrane 16 may be a single layered membrane that is fixedly attached to the wire element 18. Preferred materials for the membrane 18 include polymeric films. A suitable polymeric film is polyethylene.

Preferably, the membrane 16 is slack, as illustrated in FIG. 1. By slack is meant that the membrane forms a slight pouch or an indentation in which an organ 28 is retained. For example, the retractor device of the present invention is used to retain the bowel during deep abdominal surgery. Unlike retraction of muscle, soft tissue retraction, such as the bowel, presents a unique problem. Not only must the organ be held securely out of the way during surgery, the organ must be held in as gentle a manner as possible so that it is not damaged and circulation through the organ is not affected. The membrane provides a flexible surface, and, in the membrane's relatively slack state, an indentation or pouch is formed when the retractor is placed against the organ 28. Using the device of the present invention, the organ is gently but securely held in place, minimizing the chance of the organ sliding parallel to the retractor blade surface and out of a "retained" position. Although preferably the membrane 16 is in a slack state, the membrane could be taut, that is, held under tension, and still provide adequate retraction. In such a case, the flexibility of the film provides a retraction surface that gently retains the organ.

In addition, the membrane 18 is preferably transparent so that the organ 28 is viewable through the membrane 16. By transparent is meant that the organ is sufficiently viewable so that the condition of the organ can be ascertained. For example, lack of circulation may be indicated by a discoloration of the organ. Such discoloration should be visible through the membrane.

Figures 2, 3:
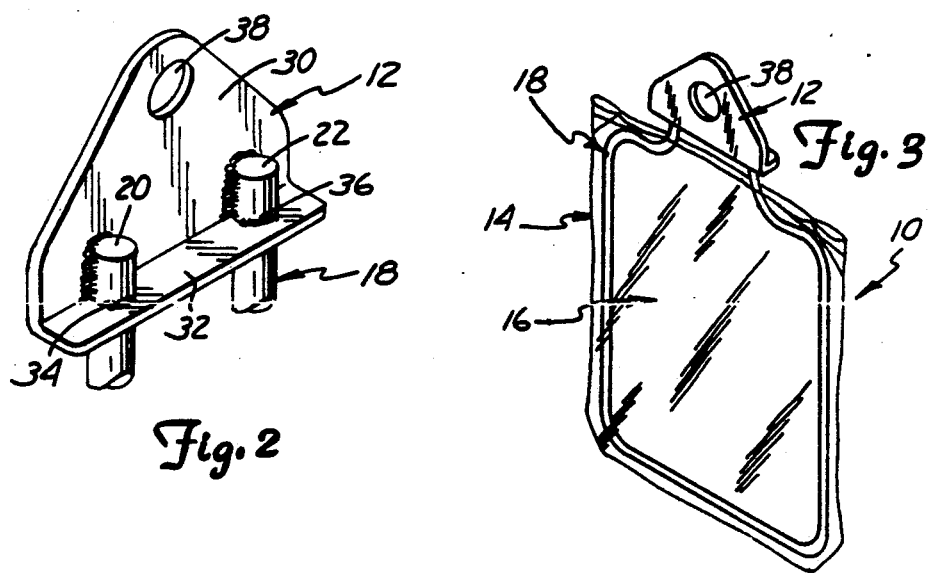
FIG. 2 is a perspective view of the support member of the retractor device of the present invention.
FIG. 3 is a perspective view of the retractor apparatus of the present invention in a flat state.

To further aid in holding the organ, the wire element 18 is made of a malleable material. By malleable is meant that the wire element is bendable and then stays bent in the selected shape or form in which it is bent. As illustrated in FIG. 3, the blade of the retractor device of the present invention is initially in a flat state. The surgeon then bends the wire element to form the blade to a selected shape. It will be appreciated that each surgical procedure can be different and that the capability to form the retractor to a desired shape to the needs of a particular situation is highly desirable.

In the working embodiment illustrated in the figures, the wire element is made of stainless steel and can be sterilized for repetitive use. In an alternative embodiment, the wire element may be made of metal other than stainless steel and then coated. For example, the wire element, along with the support member 12, are encased entirely in a polymeric resin, such as polyvinyl chloride or an epoxy resin. In addition, a foamed resin coating may be applied to the wire element. Coating the wire element and the support member 12 in a plastic resin permits usage of material much less expensive than stainless steel, making the device of the present invention a disposable item.

The support member 12 is made of flat sheet metal and has a main portion 30 and secondary portion 32 disposed at approximately a right angle to the main portion 30. The portion 32 includes apertures 34 and 36 through which extend the ends 20 and 22 of the wire element 18. The apertures 34 and 36 are located adjacent the main portion 30 such that the ends 20 and 22 can be fixedly attached to the portion 30 by welding.

The support member 12 further includes an aperture 38. The aperture 38 permits attachment of the retractor device 10 to a retractor support clamp 40, as illustrated in FIG. 1. The retractor support clamp is then held by a suitable retractor support, such as illustrated and described in the LeVahn et al U.S. Pat. No. 4,617,916, assigned to the same assignee as the present application, and herein incorporated by reference. Although the specific retractor apparatus in the LeVahn et al Patent is mentioned, any suitable retractor support can be used with the retractor device of the present invention.

Although the present invention has been described with reference to preferred embodiments, workers skilled in the art will recognize that changes may be made in form and detail without departing from the spirit and scope of the invention.

What is claimed is:

1. A retractor device for use with a retractor support and having means for attaching the retractor device to the retractor support, the device comprising:
   a retractor blade having a perimeter and including a bendable wire support member extending along the perimeter defining a blade perimeter and a retractor area, and a flexible member supported by the wire member and extending over the retractor area such that the shape of the blade is changeable.

2. The device of claim 1 wherein the member is substantially transparent.

3. The device of claim 2 wherein the flexible member is made of a flexible polymeric material.

4. The device of claim 1 wherein the flexible member is in a slack state.

5. The device of claim 4 wherein the flexible member is in a sufficiently slack state to form a pouch.

6. The device of claim 1 wherein the wire member is made of a malleable material.

7. A retractor device for use with a retractor support apparatus and having means for attachment to the retractor support apparatus, the device comprising:
   a retractor blade having a flexible pouch portion for engaging an organ, the flexible pouch portion supported by a wire perimeter.

8. The device of claim 7 wherein the flexible pouch portion is made of a polymeric film.

9. The device of claim 8 wherein the film is substantially transparent.

10. The device of claim 9 wherein the pouch portion has a perimeter defined by a malleable element, the malleable element being bendable to a selected shape.

11. The device of claim 10 wherein the malleable element is a wire.

12. A retractor device for use with a retractor support and having means for attachment to the retractor support, the device comprising:
   a retractor blade including a malleable element defining a perimeter of the retractor blade and defining a retractor area within the perimeter; and
   a flexible membrane extending over the retractor area and attached to the malleable element, the malleable element being bendable to a selected shape.

13. The device of claim 12 wherein the membrane is in a slack state.

14. The device of claim 12 wherein the membrane as in a taut state.

15. The device of claim 12 wherein the membrane is a polymeric film.

16. The device of claim 12 wherein the malleable element is a wire.

17. The device of claim 12 wherein the malleable element is a continuous loop.

18. A retractor device for use with a retractor support apparatus and having means for attachment to the retractor support apparatus, the device comprising:
   a retractor blade having a support member defining a perimeter and a retractor area and a flexible membrane attached to the support member and extending over the retractor area in a slack state.

19. The device of claim 18 wherein the membrane is made of a polymeric film.

20. The device of claim 18 wherein the membrane is substantially transparent.

21. The device of claim 18 wherein the support member is made of a malleable material such that the blade is bendable to a selected shape.

* * * * *